United States Patent [19]

Glascock

[11] Patent Number: 4,905,681
[45] Date of Patent: Mar. 6, 1990

[54] SKIN GUARD APPARATUS

[75] Inventor: Vern A. Glascock, Salt Lake City, Utah

[73] Assignee: The Glascock Family Trust, Salt Lake City, Utah ; Vern A. and Iris S. Glascock, as trustees

[21] Appl. No.: 115,370

[22] Filed: Nov. 2, 1987

[51] Int. Cl.$^4$ .................... A61F 13/00; A61F 15/00; A61L 15/00

[52] U.S. Cl. .................... 128/155; 128/157; 128/165; 128/846; 128/888; 2/9; 2/22; 604/304

[58] Field of Search ................. 604/304, 308; 128/155, 128/157, 163, 335, 846, 857, 858, 864, 866, 165, 887, 888, 889, 892, 894; 2/9, 206, 410, 417, 419, 420, 425, 22

[56] References Cited

U.S. PATENT DOCUMENTS

| 1,290,140 | 1/1919 | Elleby | 2/9 |
| 2,254,669 | 9/1941 | Turner | 2/9 |
| 3,141,459 | 7/1964 | Orcutt | 128/157 |
| 3,503,392 | 3/1970 | Beeman | 128/157 |
| 3,815,152 | 6/1974 | Bedharczuk et al. | 2/9 |
| 4,215,687 | 8/1980 | Shaw | 128/165 |

FOREIGN PATENT DOCUMENTS 0165664 3/1954 Australia .................... 128/155

OTHER PUBLICATIONS

Biobrane ® Temporary Wound Dressing Package insert; 10/85; Woodruff Labs, Inc., Santa Anna, California.

Primary Examiner—Richard J. Apley
Assistant Examiner—Paul Prebilic
Attorney, Agent, or Firm—Trask, Britt & Rossa

[57] ABSTRACT

A ventilated skin guard apparatus similar to a baseball catcher's mask or fencer's mask is disclosed. The apparatus is adjustable in size and shape and is used to prevent foreign bodies from coming into contact with damaged skin while still allowing the skin to ventilate. The apparatus comprises arcuate cage members mounted in between end support members. A method of using the apparatus is also disclosed.

8 Claims, 3 Drawing Sheets

SKIN GUARD APPARATUS

FIELD

This invention relates to a method and apparatus for protecting areas of sensitive skin. It is particularly directed to a structure for protecting grafted skin sites from contact with clothing, bedding and other objects.

BACKGROUND

The skin is often referred to as the largest organ of the human body. It surrounds the body and acts as a barrier to organisms which might cause infection. Human skin is innervated and is very sensitive to external stimuli.

Skin can be damaged in several ways. It can be abraded, burned, cut, surgically removed, etc. Damaged skin is very painful. In order to treat damaged skin, it may be necessary to implant a skin graft which, while healing, the healthy area surrounding donor and recipient sites of grafted skin can be very painful and sensitive to external stimuli for several months.

Touching grafted or otherwise damaged skin with the hand or a foreign object elicits a pain response. Even a bed sheet coming into contact with damaged or grafted skin can be very painful to a burn patient convalescing in bed.

Ventilation may be helpful in treating damaged skin. The air helps to keep the damaged skin cool, and feels refreshing to the patient.

Heretofore, methods for keeping foreign objects from contacting damaged skin have consisted of either wrapping the damaged area with gauze or cloth, or applying an artificial membrane to the damaged area.

Typical of the artificial membrane protective covers are Band-Aid ® bandages. This type of bandage is adequate for protecting relatively small areas of skin, but the bandages are too small to cover larger areas adequately. These bandages consist of a non-adhesive and generally absorbent area, surrounded on at least two sides with adhesive areas. The absorbent area is placed over the damaged skin, while the adhesive areas are preferably placed on the surrounding healthy tissue. Bandages and dressings of this type are unsuitable for sensitive graft sites which cannot tolerate physical contact. Furthermore, ventilation through gauze dressings and bandages is limited.

Woodruff Laboratories, Inc. of Santa Ana, Calif., markets a biosynthetic temporary wound dressing under the trademark Biobrane ®. The dressing is adherent and flexible, and is a biocomposite of a thin semipermeable silicone membrane mechanically bonded to a flexible knitted nylon fabric. Biobrane ® suffers the same disadvantages of other skin protection mechanisms, i.e., it does not prevent painful pressure application to the damaged area of the skin, does not allow sufficient ventilation to the damaged area, and does not allow the spray application of antiseptic or anesthetic products without removal of the mechanism. There remains a need for an apparatus with these features which is adaptable to a variety of specific emergency and outpatient applications.

SUMMARY OF THE INVENTION

This invention comprises a ventilated skin guard apparatus, and a method for using the apparatus. The apparatus comprises a cage structure adapted to attach to the body of a user or patient to enclose the sensitive area without substantially impeding air circulation adjacent to that area. The cage typically includes a plurality of arcuate members and end supports connecting the arcuate members into a rigid or semi-rigid assembly. Attachment means mount the cage assembly to a portion of the anatomy, typically an appendage. The ventilated skin guard apparatus is positioned to surround the damaged area of skin of the patient, thereby preventing objects (notably clothing or bedding) from coming into contact with the damaged area of the skin. In certain embodiments, the arcuate cage members and the end supports are adjustable in length and interconnect in various arrangements to accommodate to various sites or sizes of anatomy.

The arcuate cage members of the apparatus preferably connect parallel one to another, and are of similar size and shape. In certain embodiments, interconnecting arcuate cage members run longitudinally. In other embodiments, the arcuate cage members run laterally, approximately parallel the end supports.

Selection of either lateral or longitudinal members is dependent upon the size and shape of the damaged skin area (the "wound"). In the case of long, narrow wounds, use of lateral arcuate cage members is preferred, as these members can be interconnected or "stacked" to fashion a correspondingly long, narrow cage structure. The lengths of either or both end supports and arcuate members, whether lateral or longitudinal, may be adjustable, e.g. through the use of telescoping members or other means.

In other embodiments of the invention, the cage structure comprises a gridwork of lateral and longitudinal members which are arched and interwoven one with another, so that the cage portion of the skin guard apparatus is bowl-shaped, or parabolic.

The cage structure of the skin guard apparatus should be fashioned and mounted to the patient to avoid contact with any sensitive skin. The periphery of the cage preferably abuts healthy skin so that the arcuate cage members form a protective dome over the damaged area. At the point of contact, padding may be incorporated to increase the comfort of the patient. Mounting means may comprise tape or a strap which may be fastened about that portion of the body which carries the sensitive site (e.g. torso or limbs). It is sometimes preferred to anchor the skin guard apparatus to the patient's anatomy along a portion of the perimeter of the cage. The unattached portion of the perimeter permits relatively unrestricted movement by the patient. This mode of attachment is especially desirable when the wound occurs in a region such as the thigh, where movement tends to flex and contract the skin surface as a consequence of normal movements by the patient. As a rule, it is preferable to anchor the portion of the cage perimeter closest to the geometric center of the patient.

The structural members of the cage may be quite rigid, but generally are flexible to accommodate adjustment and shaping as needed in the field. Individual members may comprise metal, fabric, wood, plastic bands, straps, strings or other structural elements with the appropriate properties of rigidity (or semi-rigidity), pliability, light weight and durability for prolonged use. Preformed standard sizes and shapes are within contemplation, and they may remain adjustable in size and shape.

The skin guard apparatus is used by first determining the size and shape of the damaged skin area to be protected. An appropriate skin guard apparatus is selected or constructed. The apparatus is sized to the wound, and mounted around the wound so that the portion of the apparatus supported by the patient contacts only healthy skin, and the arcuate members form a dome cage over the damaged skin area. The sensitive skin area is thereby isolated from contact without impeding air ventilation or the application of medication through the apparatus to the damaged skin site.

DETAILED DESCRIPTION OF THE PREFERRED EMBODIMENTS

Figure 9:
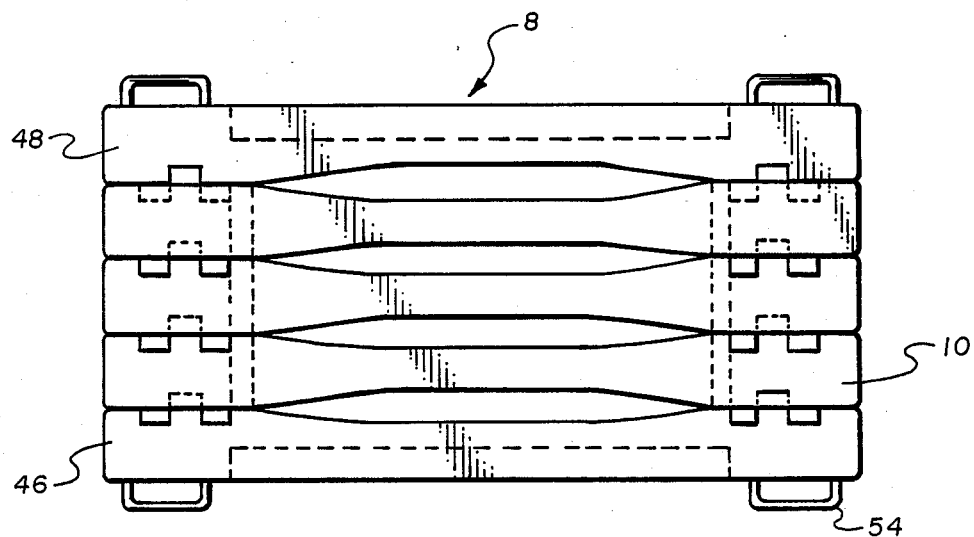
FIG. 9 is a top view of stacked longitudinal arcuate members connected to end support members of the skin guard apparatus.
Figure 10:
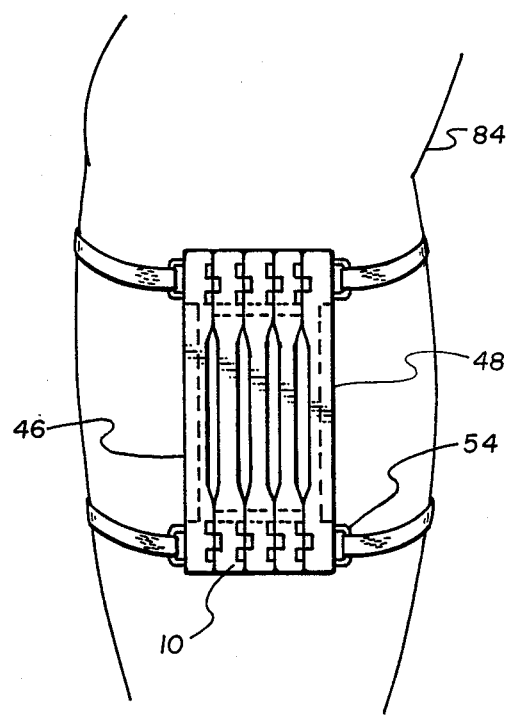
FIG. 10 depicts the stacked longitudinal arcuate members and end supports of FIG. 9 attached to a human thigh.

The skin guard apparatus of the present invention is an apparatus similar in structure and function to a baseball catcher's mask or fencer's mask (FIG. 9). The apparatus comprises a plurality of arcuate cage members 10 attached to end support members 46, 48, 82 so that when the apparatus is mounted to a patient (e.g. the limb 84 shown in FIG. 10), the arcuate cage members 10 and end supports 46, 48 form a mechanical cage, designated generally 11, in the shape of a dome (FIG. 9). This dome is fastened, as shown in FIG. 10, to isolate the sensitive damaged skin area from painful contact. The apparatus is ideal for use in skin graft patients.

The arcuate cage members of the present invention can be mounted laterally, longitudinally, or diagonally to the end support members. The cage members preferably interconnect one to another so that the ultimate size and shape of the apparatus is adjustable. In one alternative embodiment of the invention, the arcuate cage members are an interwoven network of lateral and longitudinal wire members. In embodiments where the arcuate cage members are either lateral or longitudinal, but not both, the members are connected in a parallel fashion for aesthetic reasons. All arcuate cage members 10, 72, except for the aforementioned interwoven device may be adjustable in area if desired.

Figure 1:
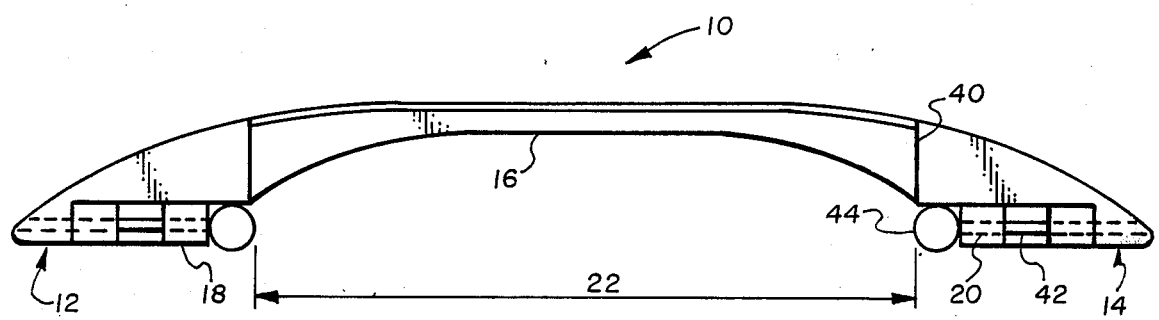
FIG. 1 is a side view of a longitudinal arcuate cage member.
Figure 2:
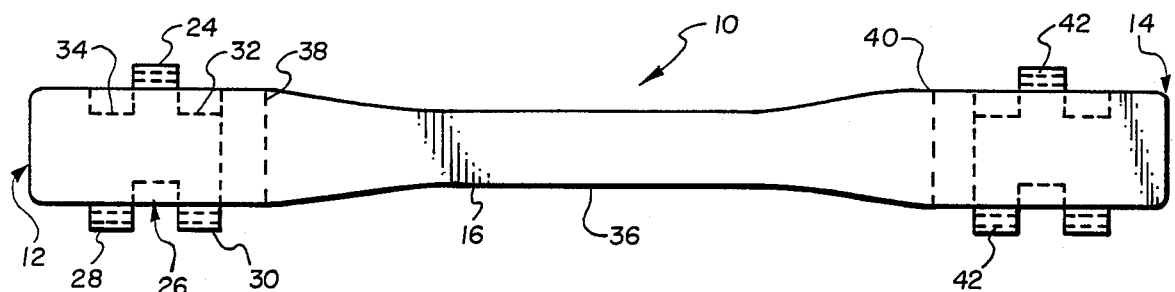
FIG. 2 is a top view of the longitudinal arcuate cage member of FIG. 1.

The longitudinal arcuate cage member 10 depicted in FIGS. 1 and 2 are typical of those used in the present invention. The longitudinal arcuate cage members 10 of FIG. 1 consist of two base supports 12, 14 positioned on either side of a spanning arch 16. The bottom surfaces 18, 20 of the base supports 12, 14 are designed to contact the patient's skin, while the length 22 of the arch 16 is sized to span the damaged area of skin. Typical lengths 22 of arch 16 vary from about five inches (12.7 cm) to about eleven inches (27.8 cm).

The use of the arch shape in the arcuate cage member 10 allows for strong structural support, but still prevents contact with the damaged area of skin.

On each base support 12, 14 means for interlocking or interconnecting the arcuate cage members 10 may be mounted. The arcuate cage members (10) are distinct units which are separably interchangeable with one another. In FIG. 2 a tongue and groove model is disclosed. The tongue 24 of base support 12 of arcuate cage member 10 is sized to fit into the groove 26 of another arcuate cage member 10A (FIGS. 2 and 9). When the tongue 24 is inserted into the groove 26 of another arcuate cage member 10A, the sidewalls 28, 30 in effect form two other tongues which fit within other grooves 32, 34 of the other arcuate cage member. As depicted, the other base support 14 has identical means for interconnecting the arcuate cage members so that the longitudinal arcuate cage members of FIGS. 1 and 2 can be interconnected ("stacked") one to another to any desired size. The size of the cage 11 is dependent on the number of arcuate cage members 10 used, taking into consideration the width and length of the end support members 46, 48.

As can be seen in FIG. 2, the arch 16 tapers inwardly, being narrower at its center 36 (e.g. approximately ½ inch), than at its ends 38, 40 (e.g. approximately ¾ inch). At its ends, the arch 16 connects with the base supports 12, 14. This tapering creates apertures 19 in stacked cage members 10 which allow air to ventilate through the arcuate cage members. These apertures 19 also allow for the spray application of various topical agents (e.g. antiseptics and anesthetics) without removing the entire apparatus.

To keep the arcuate cage members 10 in place once stacked, a hole 42 may be drilled through the interconnection means, and a pin 44 placed therethrough to keep the stacked members interconnected (FIG. 1). Instead of a pin, a screw, glue or other means might be used to keep the arcuate cage members positioned properly.

In a preferred embodiment, foam rubber or some other soft padding is placed on the bottom surfaces 18, 20 of the base supports 12, 14 to increase user comfort.

In another embodiment the arch 16 is adjustable in length 22 so that one construction of arcuate cage member can be adjusted to cover any size, within a range, of wound. Telescoping arches or arches consisting of two separate pieces connected by a nut and bolt assembly may be used to accomplish the adjustable length feature.

The arcuate cage members 10 and end support members 46 and 48 may be integrally formed or assembled from separate pieces. The arcuate cage members 10 and end support members 46, 48 may be constructed of any durable, stiff material.

Figure 3:
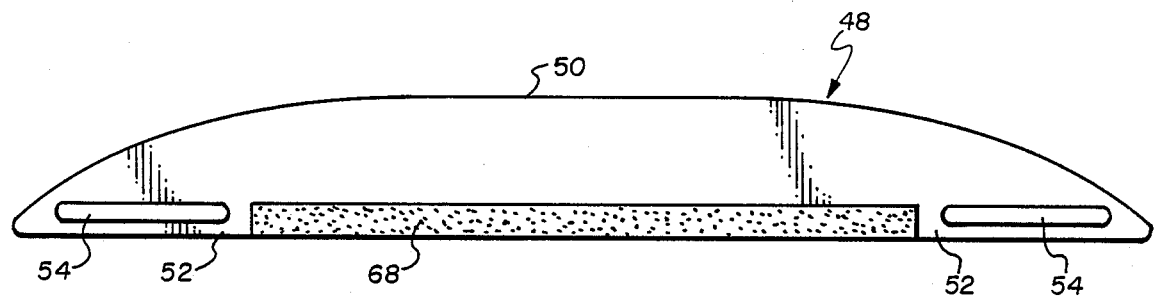
FIG. 3 is a side view of an end support member.

FIG. 3 depicts the outside surface of end support member 46, opposite end support member 48 or alternative end support 82. The end support members 46, 48, 82 comprise a frame member 50 having a bottom surface 52, mounting or attaching means 54; and means for connecting the end support members 46, 48, 82 to the stacked arcuate cage members 10.

Figure 4:
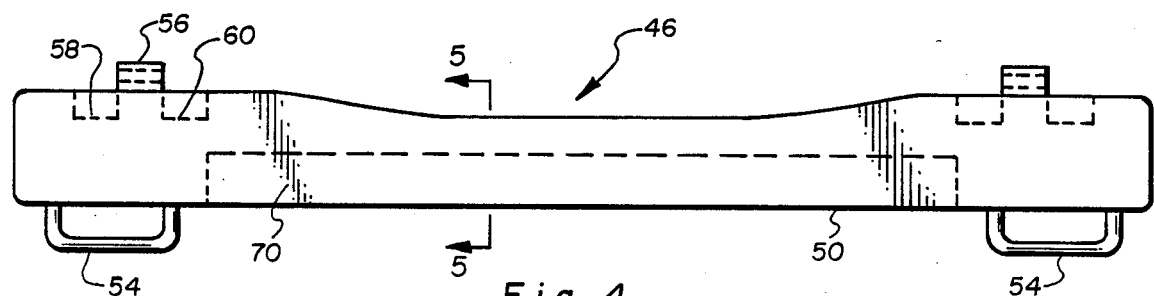
FIG. 4 is a top view of the end support member of FIG. 3 or FIG. 6.
Figure 6:
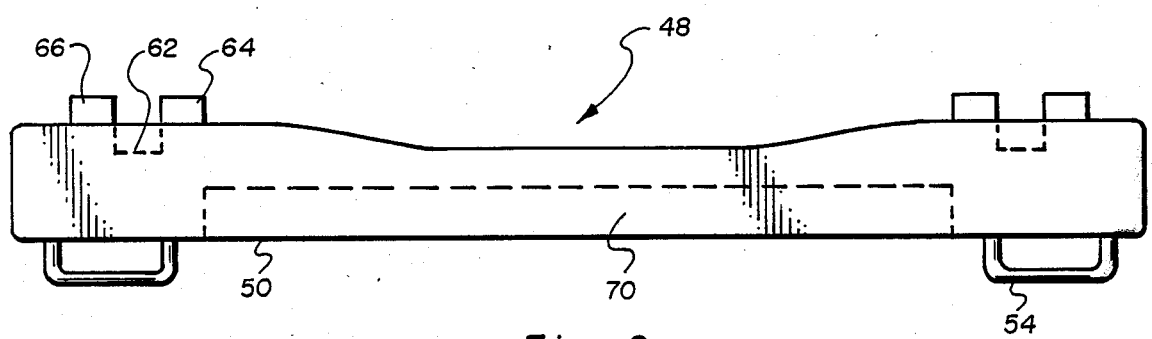
FIG. 6 is a top view of an end support member.

Means for connecting the end support members 46, 48, 82 to the arcuate cage members 10 are shown in FIGS. 4 and 6. The connection means of end support member 46 is identical to one-half of the interconnecting means of arcuate cage member 10 depicted in FIG.

2. End support member 46 has a tongue 56 analogous to tongue 24. End support member 46 also has grooves 58, 60 analogous to the grooves 32, 34 of the arcuate cage member 10. Tongue 56 is sized to fit within groove 26 of the arcuate cage member 10. When tongue 56 is inserted into groove 26, the sidewalls 28, 30 fit into the grooves 58, 60 of end support member 46, so that the end support member is connected to the arcuate cage member 10. The opposite connecting means of end support member 46 fits into the interconnecting means of base support 14 of arcuate cage member 10.

Referring now to FIG. 6, the connection means of end support member 48 is identical to the other half of the interconnecting means of arcuate cage member 10. End support member 48 has a groove 62 analogous to groove 26 of the arcuate cage member 10. End support member 48 also has sidewalls 64, 66 analogous to the sidewalls 28, 30 of the arcuate cage member 10. The tongue 24 of an arcuate cage member is sized to fit into the groove 62 of the end support member 48. When the tongue 24 is inserted into groove 62, the sidewalls 64, 66 fit into the grooves 32, 34 of the arcuate cage member 10.

In essence, the end support members 46, 48 "sandwich" the arcuate cage members (FIGS. 9 and 10). As few as one arcuate cage member 10 can be sandwiched by the end support members 46, 48. As before, the tongue 56, sidewalls 64, 66 and grooves 58, 60, 62 of the end support members 46, 48, 82 can contain a hole similar to hole 42 for pin 44 placement.

Figure 5:
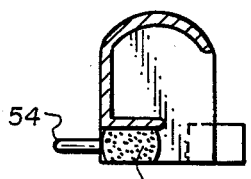
FIG. 5 is a cross-sectional view of the end support member of FIG. 3 taken along section line 5—5 of FIG. 4.

The mounting means 54 disclosed in FIGS. 5 and 6 is an open loop attached to the end support members 46, 48, 82. A strap 47 (FIG. 10) can be put through the loop 54 and connected around that body portion 84 of the patient which contains the damaged skin (e.g. the skin guard apparatus can be strapped around a patient's leg if that is where the damaged skin area is.)

In one embodiment, only the mounting means 54 closest the spine of the patient is used. For example, only the top of the skin guard apparatus may be strapped around the leg of the user. Such an arrangement allows for relatively freer movement by the patient.

FIG. 5 depicts a cross-sectional view of end support member 46 taken along section line 5—5 (FIG. 4). Absorbent and/or soft material 68 may be placed inside of indentation 70 (FIGS. 3 and 4). This material adds to patient comfort by supplying a softer surface in contact with the skin. The absorbency sponges up liquids, helping to keep the wound dry.

Figure 7:
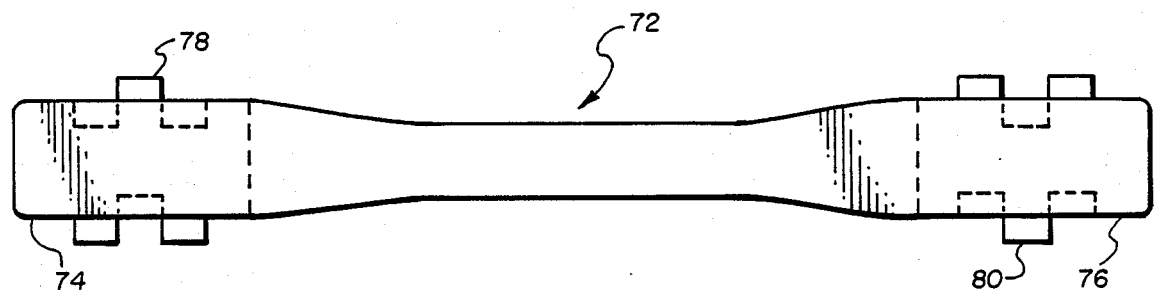
FIG. 7 is a top view of an alternative longitudinal arcuate cage member.

In an alternative embodiment, the interconnecting means of the arcuate cage member 72 are staggered (FIG. 7). One base support 74 of the arcuate cage member 72 is identical to the base support 12 of arcuate cage member 10 (FIG. 2). The other base support member 76 of arcuate cage member 72 is also identical to base support 12, but it has been reversed or turned upside down, so that the tongue 78 of base support 74 extends in an opposite direction to the tongue 80 of base support 76. Using such an arrangement, these arcuate cage members 72 still interconnect or stack one in another in a fashion similar to the aforementioned arcuate cage members 10. The advantage of such an embodiment is that only one type of end support member 82 need be fashioned to encase both sides of the arcuate cage members 72. One end support member design will work on either side of the arcuate cage members, even though two end support members 82 will still be required.

Figure 8:
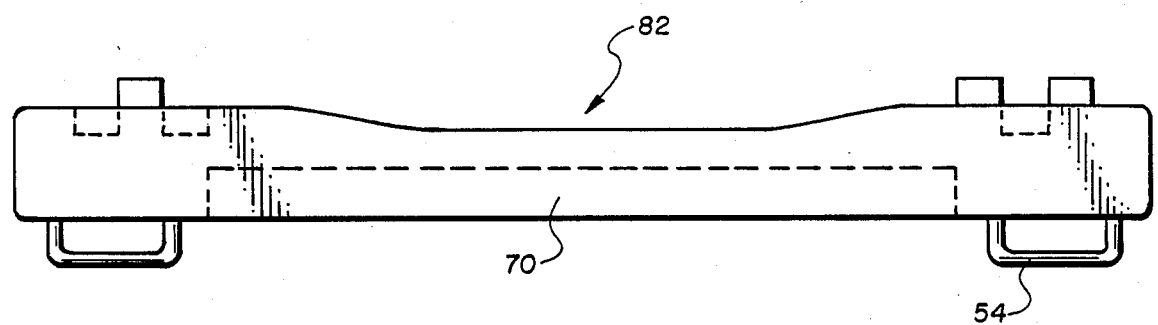
FIG. 8 is a top view of an alternative end support member.

The end support member 82 of this alternative embodiment (FIG. 8) works identically with the end support members 46, 48 previously described. A tongue side 83 of the connecting means of end support member 82 is inserted into the groove side 74 of an external arcuate cage member 72. The groove side 85 of the connecting means of end support member 82 is inserted into the tongue side 76 of an external arcuate cage member 72. As in the previously described embodiments, the apparatus can be more permanently connected by means of glue, screws, pins, etc.

Those skilled in the art will recognize that various other structures are possible without departing from the intended scope of this invention. For example, the arcuate cage members may be laterally placed in between two longitudinal end support members to create an apparatus having a ladder-like arrangement (not shown). Such an arrangement would be ideal for protecting long narrow areas of damaged skin. The longer the wound, the greater number of arcuate cage members and greater length of end support members used.

Another possible arrangement involves the use of arcuate cage members placed diagonally in between longitudinal end support members. These members could overlap one with another providing extra prevention.

Alternatively, interwoven wire, such as "chickenwire," or other type of mesh or screening might be placed in between the end support members. Also, a ring or annular framework of a size sufficient to surround the wound could be made and the interwoven wire attached to the framework and shaped into a dome covering the wound which would protect the underlying sensitive skin from contact with foreign objects. At least three contact points with the skin would be preferred for stability.

Whatever the particular apparatus, all apparati are used generally in the same way.

First, the size and shape of the wound is determined, and an appropriate style of skin guard apparatus chosen. For box shaped or circular wounds the skin guard apparatus using longitudinal arcuate cage members may be used.

Second, the number of arcuate cage members are chosen. The wider the wound, and hence the greater the needed size of skin guard apparatus, the more arcuate cage members are needed. The apparatus is assembled and connected as desired.

Third, the apparatus is placed onto the user so that the portion of the skin guard apparatus placed onto the user's skin preferably only contacts healthy skin, while the arcuate cage members form a dome over the sensitive skin area. The dome should not contact the skin, but should protect the skin from foreign objects which might come into contact with the skin.

Fourth, the apparatus is mounted or attached to the user (FIG. 10). Adjustable straps 47 connected to the apparatus which surround the body member 84 (e.g. limb or torso) are ideal for attaching the apparatus to the user. If desired, only the portion of the apparatus nearest the center of the body can be attached so as to allow more freedom of movement for the user.

The skin guard apparatus can then be left on while the wound is healing. Topical preparations can be sprayed through the apertures 19. Air ventilates the wound naturally. The skin guard apparatus can be easily removed to treat the area (e.g. for debridement), and then be remounted.

Reference herein to specific details or certain embodiments is not intended to limit the scope of the appended claims.

I claim:

1. A ventilated skin guard apparatus for protecting an area of damaged skin comprising: two elongate end support members;
   an elongate arcuate cage member distinct from the two elongate end support members, interposed between said elongate end support members, parallel to said end support members, and adapted to connect to said elongate end support members;
   means for interlocking in a tongue and groove fashion said elongate arcuate cage member to other elongate arcuate cage members and to said elongate and support members so that when said elongate arcuate cage member is interlocked with said elongate end support members, apertures are formed; and
   means for attaching said elongate arcuate cage member interlocked with said elongate end support members around the damaged skin of a user, so that when said skin guard apparatus is attached to a user, the damaged skin underneath said skin guard apparatus is protected from physical contact with objects, while air passes through said apertures.

2. The ventilated skin guard apparatus of claim 1 wherein said elongate arcuate cage member and said elongate end support members are adjustable in length.

3. The ventilated skin guard apparatus of claim 2 wherein said means for attaching said elongate arcuate cage member interlocked with said elongate end support members to said user is by means of a strap attached around a portion of the body of the user.

4. A ventilated skin guard apparatus for protecting an area of damaged skin said area of damaged skin having a periphery, said apparatus comprising:
   a plurality of elongate arcuate cage members, said members being distinct units separably interchangeable with one another;
   two distinct longitudinal elongate end support members adapted to connect said elongate arcuate cage members;
   means placed at both ends of the elongate arcuate cage members for fixedly connecting said elongate arcuate cage members to one another and for connecting said elongate cage members to said distinct longitudinal elongate en d support members; and
   means for mounting interconnected elongate arcuate cage members and connected distinct longitudinal elongate end support members around said periphery, so that when said guard apparatus is so mounted, the elongate arcuate cage members prevent foreign objects from coming into contact with the damaged skin and allow air to contact the damaged skin and the skin guard apparatus forms a mechanical cage in the shape of a dome over the damaged skin.

5. The ventilated skin guard apparatus of claim 4 wherein said longitudinal end support members are adjustable in length.

6. The ventilated skin guard apparatus of claim 5 wherein said means for mounting said interlocked arcuate cage member and end support members to the user is by a strap surrounding a portion of the body of the user.

7. The ventilated skin guard apparatus of claim 6 further including padding means attached to said elongate end support member, wherein said padding means covers said elongated end support member at points where said skin guard apparatus contact said user.

8. The ventilated skin guard apparatus of claim 4 wherein said elongate arcuate cage members are lateral arcuate cage members.

* * * * *